US009924989B2

(12) United States Patent
Dix

(10) Patent No.: US 9,924,989 B2
(45) Date of Patent: *Mar. 27, 2018

(54) MINIMALLY INVASIVE SPINAL FUSION SYSTEM AND METHOD

(71) Applicant: ZynFusion, LLC, San Antonio, TX (US)

(72) Inventor: James Earl Dix, San Antonio, TX (US)

(73) Assignee: ZYNFUSION, LLC, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/299,227

(22) Filed: Oct. 20, 2016

(65) Prior Publication Data

US 2017/0035484 A1 Feb. 9, 2017

Related U.S. Application Data

(63) Continuation of application No. 14/789,805, filed on Jul. 1, 2015, now Pat. No. 9,498,348, which is a (Continued)

(51) Int. Cl.
*A61B 17/80* (2006.01)
*A61B 17/88* (2006.01)
(Continued)

(52) U.S. Cl.
CPC .... *A61B 17/8805* (2013.01); *A61B 17/00234* (2013.01); *A61B 17/7061* (2013.01);
(Continued)

(58) Field of Classification Search
CPC ............ A61F 2/441; A61F 2002/30579; A61F 2002/30583; A61F 2002/30581;
(Continued)

(56) References Cited

U.S. PATENT DOCUMENTS 6,558,390 B2   5/2003  Cragg
6,805,697 B1  10/2004  Helm et al.
(Continued)

FOREIGN PATENT DOCUMENTS

RU        2456947       7/2012
WO    WO 2011/082499    7/2011

OTHER PUBLICATIONS

Search Report and Written Opinion in PCT Application No. PCT/US2015/045033 dated Oct. 29, 2015 in 8 pages.
(Continued)

*Primary Examiner* — Eduardo C Robert
*Assistant Examiner* — Tara R Carter
(74) *Attorney, Agent, or Firm* — Knobbe Martens Olson & Bear LLP

(57) ABSTRACT

Disclosed herein are minimally invasive systems and method for stabilizing the spine, while preserving a degree of spinal flexion and extension of the spine at the level of the stabilized vertebrae postoperatively. The systems and methods can include an expandable anchor and rod that span an intervertebral disc. The anchor can have interstices, and ends in two adjacent vertebral bodies. The system can also include a volume of bone cement media.

19 Claims, 7 Drawing Sheets

Related U.S. Application Data continuation of application No. 14/559,071, filed on Dec. 3, 2014, now Pat. No. 9,101,408.

(60) Provisional application No. 62/039,863, filed on Aug. 20, 2014.

(51) Int. Cl.
| | | |
|---|---|---|
| *A61B 17/70* | (2006.01) | |
| *A61F 2/44* | (2006.01) | |
| *A61F 2/46* | (2006.01) | |
| *A61B 17/00* | (2006.01) | |

(52) U.S. Cl.
CPC ...... *A61B 17/7083* (2013.01); *A61B 17/7098* (2013.01); *A61F 2/442* (2013.01); *A61F 2/4455* (2013.01); *A61F 2/4611* (2013.01); *A61B 2017/00933* (2013.01); *A61B 2017/00955* (2013.01); *A61F 2002/4475* (2013.01)

(58) Field of Classification Search
CPC .... A61F 2210/0085; A61F 2002/30586; A61F 2/4455; A61F 2002/448; A61F 2002/30019; A61F 2/4601
USPC .......... 606/246–249, 92–94, 300, 304, 323, 606/62–68; 623/17.11–17.16
See application file for complete search history.

(56) References Cited

U.S. PATENT DOCUMENTS

| | | |
|---|---|---|
| 7,241,297 B2 | 7/2007 | Shaolian et al. |
| 7,749,267 B2 | 7/2010 | Karmon |
| 8,021,401 B2 | 9/2011 | Carl et al. |
| 8,277,506 B2 | 10/2012 | Krueger et al. |
| 8,317,867 B2 | 11/2012 | Cragg |
| 8,357,198 B2 | 1/2013 | McGraw et al. |
| 8,382,837 B2 | 2/2013 | Sennett et al. |
| 8,579,903 B2 | 11/2013 | Carl |
| 9,101,408 B1 | 8/2015 | Dix |
| 9,498,348 B2 | 11/2016 | Dix |
| 2007/0027545 A1* | 2/2007 | Carls ............ A61B 17/70 623/17.12 |
| 2008/0086133 A1 | 4/2008 | Kuslich et al. |
| 2009/0112221 A1* | 4/2009 | Burke ............ A61F 2/4657 606/102 |
| 2009/0182386 A1 | 7/2009 | Schaller |
| 2010/0262240 A1* | 10/2010 | Chavatte ........ A61B 17/7098 623/17.11 |
| 2011/0046737 A1* | 2/2011 | Teisen ............ A61B 17/8872 623/17.11 |
| 2014/0046245 A1 | 2/2014 | Cornacchia |
| 2016/0051375 A1 | 2/2016 | Dix |

OTHER PUBLICATIONS

Yu, Chia-Wei, et al. "Percutaneous balloon kyphoplasty for the treatment of vertebral compression fractures." BMC surgery 14.1 (2014): 3. In 6 pages.

* cited by examiner

MINIMALLY INVASIVE SPINAL FUSION SYSTEM AND METHOD

PRIORITY CLAIM

This application claims the benefit under 35 U.S.C. § 120 as a continuation application of U.S. patent application Ser. No. 14/789,805 filed on Jul. 1, 2015, which is in turn a continuation of U.S. patent application Ser. No. 14/559,071 filed on Dec. 3, 2014 and now issued as U.S. Pat. No. 9,101,408, which in turn claims the benefit under 35 U.S.C. § 119(e) as a nonprovisional application of U.S. Prov. App. No. 62/039,863 filed on Aug. 20, 2014. Each of the foregoing priority applications are hereby incorporated by reference in their entireties.

BACKGROUND

Most spinal fusions are performed for patients with back pain with or without radicular symptoms (radiating pain) or neurogenic claudication (pain with walking) caused by degenerative disc disease (spondylosis). Roughly 90% of all spine surgeries involve fusion. Over 465,000 spinal fusions were performed in 2011 in the US at a cost of nearly 13 billion dollars.

Not to be limited by theory, pain from such pathology is believed to be caused by abnormal motion (instability). Fusion is performed to reduce or eliminate the motion of the degenerated disc segment by immobilizing the adjacent vertebral bodies. The majority of spinal fusions are performed with a posterolateral approach with bone graft material placed across the facets, lamina and transverse processes. A combination of transpedicular screws and connecting rods or plates provide immobilization of the vertebra until the bone graft material can form a solid bony fusion mass. A growing number of fusions are performed with an anterior approach with the bone graft placed in the disc space to allow bony fusion of the vertebral bodies across the disc space. Anterior fusions are typically performed in conjunction with posterolateral fusion rods to provide the immobilization needed for the bony fusion across the disc to occur. Bony fusion may take 6-12 months and fusion failure rates of 10-40% are reported in the literature.

SUMMARY

Disclosed herein are minimally invasive systems and methods for stabilizing a spine. In some embodiments, a method for stabilizing the spine includes one or more of the following steps: creating a pedicular access channel in a pedicle to access the interior of a first vertebral body; inserting an introducer cannula into the pedicle; inserting a hollow needle through a central lumen of the introducer cannula into the interior of the first vertebral body, through an intervertebral disc, and into the interior of a second vertebral body adjacent the first vertebral body; inserting an anchor through a central lumen of the hollow needle such that a distal end of the anchor is within the interior of the second vertebral body, a proximal end of the anchor is within the interior of the first vertebral body, and a central portion of the anchor spans the intervertebral disc; expanding the distal end of the anchor within the interior of the second vertebral body; expanding the proximal end of the anchor within the interior of the first vertebral body; flowing a first volume of bone cement media into the distal end of the anchor within the interior of the second vertebral body; flowing a second volume of bone cement media into the proximal end of the anchor within the interior of the first vertebral body; inserting a flexible rod through the central lumen of the hollow needle, such that a distal portion of the flexible rod is positioned within the interior of the second vertebral body and in contact with the first volume of bone cement media, the proximal portion of the flexible rod is positioned within the interior of the first vertebral body, and a central portion of the rod spans the intervertebral disc, wherein the flexible rod resides at least partially within an interior of the anchor. In some embodiments, substantially no bone cement media flows within the intervertebral disc. In some embodiments, the method does not involve a discectomy procedure. The bone cement media can include PMNIA, for example, such as between about 1 cc and 5 cc, or about 2 cc and about 3 cc. The flexible rod can comprise a carbon fiber material, such as PEEK. Expanding the distal end of the anchor within the interior of the second vertebral body and expanding the proximal end of the anchor within the interior of the first vertebral body can comprise expanding a balloon. In some embodiments, inserting the anchor step comprises inserting the anchor carried proximate the distal end of a balloon catheter. In some embodiments, a central portion of the anchor is not expanded, and the distal and proximal expanded portions of the anchor have a maximal expanded diameter that is at least 1.5×, 2×, 3×, or more of the unexpanded diameter of the central portion of the anchor. The anchor can comprise a shape memory material, such as Nitinol. The anchor can be inserted in a compressed, substantially tubular configuration. The introducer cannula can have a diameter of, for example, between about 8 Gauge to about 12 Gauge. Following insertion of the flexible rod the first and second volumes of bone cement media harden, fixing the anchor and flexible rod in place. In some embodiments, flowing the second volume occurs after the inserting a flexible rod step, such that the proximal end of the flexible rod is in contact with the second volume of bone cement media after the flowing the second volume step.

Also disclosed herein is a system for stabilizing the spine. The system can include, for example: an anchor having a proximal end, a distal end, and a central portion, the anchor having a compressed tubular configuration and an expanded configuration wherein the proximal end and the distal end of the anchor are expanded while the central portion of the anchor is not expanded, wherein the proximal end and the distal end of the anchor have maximal expanded diameters at their widest portions of at least about 2× the diameter of the central portion of the anchor, wherein the anchor is sized and configured such that the proximal end of the anchor can reside within the interior of a first vertebrae, the distal end of the anchor can reside within the interior of a second vertebrae adjacent the first vertebrae, and the central portion of the anchor spans an intervertebral disc between the first vertebrae and the second vertebrae, wherein the anchor is defined by a shape memory frame and interstices within the frame; and a flexible carbon fiber rod dimensioned to fit within an interior of the anchor, such that when implanted the flexible rod is configured to reside substantially within the anchor, wherein the distal end of the flexible rod is configured to reside within the distal end of the anchor within the interior of the second vertebrae, the proximal end of the flexible rod is configured to reside within the proximal end of the anchor within the interior of the first vertebrae and the central portion of the anchor is configured to span an intervertebral disc between the first vertebrae and the second vertebrae. The flexible carbon fiber rod comprises PEEK in some cases. When implanted, the flexible carbon fiber rod is configured to allow for at least 15 degrees, 30 degrees, or more of flexion of a patient's spine. In some embodiments, the system also includes a balloon catheter comprising a balloon configured to expand the proximal end and the distal end of the anchor. The anchor can be carried on a distal end of the balloon catheter. The system can also include a volume of bone cement media, such as PMMA. The system can also include an introducer cannula comprising a central lumen and a stylet configured to reside at least partially within the central lumen of the introducer cannula. The system can also include a curvable hollow needle comprising a central lumen configured to reside at least partially within the central lumen of the introducer cannula. The system can also include an injector needle in some embodiments.

DETAILED DESCRIPTION

Figure 1A:
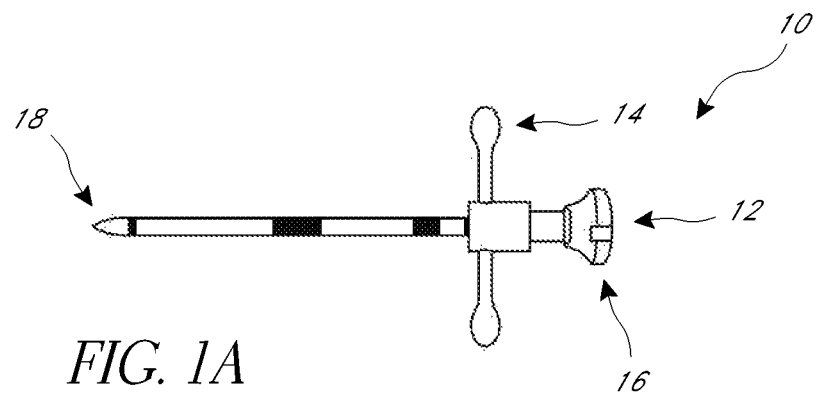
FIG. 1A illustrates an access cannula that can be part of a spinal stabilization system, in some embodiments.
Figure 1B:
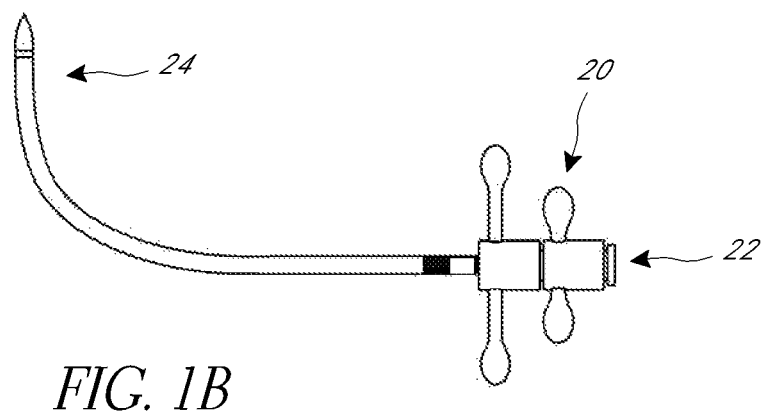
FIG. 1B illustrates a hollow curvable needle that can be part of a spinal stabilization system, in some embodiments.

Because of the high morbidity and high cost of the current methods of spinal fusion, an effective, less invasive spinal fusion at lower cost would be a significant improvement. The proposed method of spinal fusion could be done percutaneously as an outpatient rather than as an open surgical procedure which typically requires a several day inpatient stay.

Systems and methods disclosed herein can, in some embodiments, involve currently available materials approved by the FDA for human use, as well as materials that could be approved at a later date. The implanted material can include, for example, one, two, or more sources of media, including bone cement material such as PMMA (polymethylmethacrylate), a shape memory material such as the superelastic memory alloy nitinol (nickel titanium), and a polymer, including carbon reinforced PEEK (polyether ether ketone), and/or organic thermoplastic polymer. PMMA is extremely resistant to compressive stress. PMMA bone cement can be made from methylmethacrylate, polymethylmethacrylate, esters of methacrylic acid, or copolymers containing polymethylmethacrylate and polystyrene. Carbon fiber reinforced polymers such as PEEK are extremely resistant to bending stress. Nitinol (nickel titanium alloy) is a shape memory alloy resistant to repetitive bending stress.

Candidates for conventional spinal fusion can benefit from the systems and methods disclosed herein. The fusion can involve cervical, thoracic, lumbar, and/or sacral vertebrae in some embodiments. In some embodiments, a subgroup of patients who may especially benefit are older patients with osteoporosis who are poor surgical candidates and have few options for treatment.

Systems and methods for spinal fusion or stabilization are described herein. Various non-limiting embodiments of elements that can be used within systems and methods herein are illustrated in FIGS. 1A-1F. The system can include, in some embodiments, an access cannula 10 having a proximal end 16, a handle 14, and a distal end 18 with a central lumen 12 (shown in FIG. 1A) with at least one input port and exit port. The central lumen 12 of the access cannula 10 can house an inner stylet (not shown) therethrough. The system can also include a curvable needle 20 having a distal end 24, with a central lumen 22 (shown in FIG. 1B) configured to fit within the central lumen 12 of the access cannula 10, and a perforated anchor 30 having a central lumen, a first end, a second end, and an elongate section between the first and the second end. The access cannula 10 and/or the curvable needle 12 can have indicia along its length which can be radiopaque markers in some embodiments.

Figure 1C:
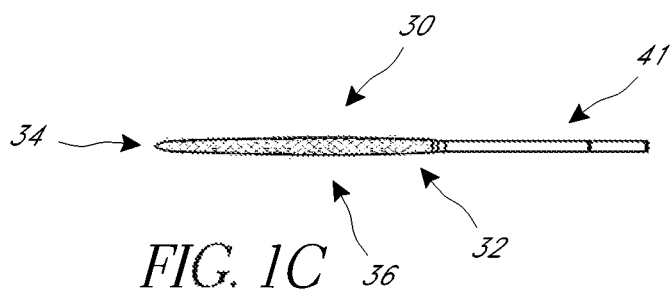
FIG. 1C illustrates an anchor carried by a balloon catheter that can be part of a spinal stabilization system, in some embodiments.

The anchor 30 is shown in FIG. 1C in a radially compressed, generally tubular configuration, and can be sized and configured to be placed within the central lumen 12 of the access cannula 10 for delivery into the spine, and mounted over the distal end of a high-pressure balloon catheter 41 or other expandable member in some embodiments. The anchor 30 can include perforations or cells sized and configured to allow for the passage of liquid bone cement therethrough, while allowing preventing passage of bone cement after hardening (e.g., solid cement) which remains confined within the anchor 30. The perforations or cells can be laser cut or otherwise created within the anchor 30. The first end 32 and the second end 34 of the anchor 30 can each include one or more discrete radially and/or axially expandable sections, such as a self-expandable or balloon-expandable section. In some embodiments, the expandable first end 32 and second end 34 can be expanded in diameter to about or at least about 1.25×, 1.5×, 1.75×, 2×, 3×, 4×, 5×, 6×, 7×, 8×, 9×, 10×, or more relative to the unexpanded diameter of the anchor 30. In some embodiments, the central elongate section 36 of the anchor is non-expandable or expandable/expanded to a lesser degree than the end sections 32, 34. The anchor 30 can be made of, for example, a metal or metallic alloy, such as a shape memory material such as nitinol or Elgiloy for example, stainless steel, and/or a polymer (including biodegradable polymers) or other materials in other embodiments. The anchor 30 can be sized and configured such that the first end 32 is contained within the cancellous bone of a first vertebrae, the second end 34 is contained within the cancellous bone of a second vertebrae adjacent the first vertebrae (either in a cephalad or caudal direction), and the elongate section 36 spans an intervertebral disc between the first and second vertebrae.

Figure 1D:
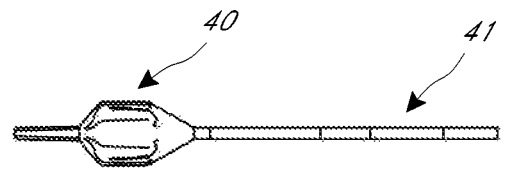
FIG. 1D illustrates a balloon catheter that can be part of a spinal stabilization system, in some embodiments.

As illustrated in FIG. 1D, the system can also include one, two, or more expandable members such as a balloon 40 on or proximate the distal end of balloon catheter 41 and configured to radially expand the anchor. In some embodiments the expandable member has sufficient strength to create a cavity within the cancellous bone as well. In some embodiments, the balloon 40 can be inflated to an inflation pressure of about or at least about 15 atm, 20 atm, 25 atm, 30 atm, or more.

Figure 1E:
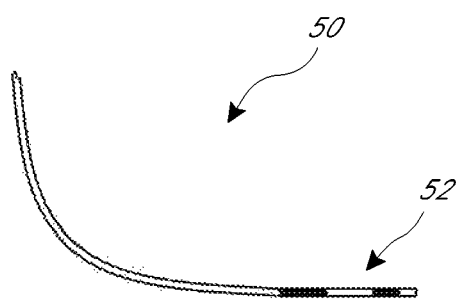
FIG. 1E illustrates a curvable media injector that can be part of a spinal stabilization system, in some embodiments.

The system can also include a cement injection needle 50 which can have a distal steerable and/or curvable portion in some embodiments as illustrated in FIG. 1E. The injection needle 50 (as well as curvable needle 20) can have a bent or curved unstressed state (e.g., made of a shape memory material) that is substantially straight while housed within a tube/sheath having sufficient column strength, but assumes its unstressed state upon advancing out of, or withdrawal of the tube/sheath. In some embodiments, the needle 50 is steerable and curvable by, for example, the use of one, two, or more pullwires operably connected to the distal end of the needle 50 and operably connected proximally to an adjustment control, such as a wheel, dial, or other element that can be adjusted by the physician to adjust the tension on the pullwire(s) and thus adjust the degree of curvature of the distal end of the needle 50, such as through a working range. The needle 50 can include one, two, or more distally facing and/or laterally facing exit ports for delivery of the cement or other media to a location within the cancellous bone.

Figure 1F:
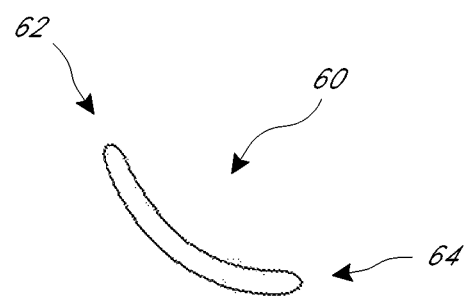
FIG. 1F illustrates a flexible carbon fiber rod that can be part of a spinal stabilization system, in some embodiments.

As illustrated in FIG. 1F, the system can also include one, two, or more flexible rods 60 with first end 62 and second end 64, such as carbon fiber rods configured to be at least partially or completely housed within the central lumen of the anchor. In some embodiments the rods 60 are sufficiently flexible to not substantially hinder flexion or extension of the spine when implanted into a patient. As noted above, the rods may be made of PEEK, carbon fiber PEEK, polyetherketoneketone (PEKK), polysulfone, polyetherimide, polyimide, ultra-high molecular weight polyethylene (UHMWPE), cross-linked UHMWPE, nano-material reinforced polymers, another medical grade polymer material, or a hybrid metal-polymer rod in some embodiments. In some embodiments, the rods are sized and configured to span no more than a single intervertebral disc (although the rods could be sized and configured to span multiple discs in other embodiments), and can be from about 1 mm to about 3 mm in diameter in some cases, such as about 2 mm in diameter.

The spinal stabilization system can also include one, two, or more volumes of media for injection into the cancellous bone. The media could include, for example, one, two, or more bone cement materials such as PMMA, for injecting into the first and second end of the anchor to stabilize the anchor within adjacent vertebrae. In some embodiments the media could be injected in a liquid or gel-like state that hardens or otherwise solidifies some time after injection into the vertebral cavity. The media could also include, for example, bone growth material, stem cells, and/or one, two, or more other therapeutic agents, such as a growth factor, anesthetic agent, steroid or other anti-inflammatory agent, narcotic or non-narcotic pain control agent, an antibiotic, an antibody, an anti-cancer chemotherapeutic agent, radiation-emitting materials, and the like.

Figure 2A:
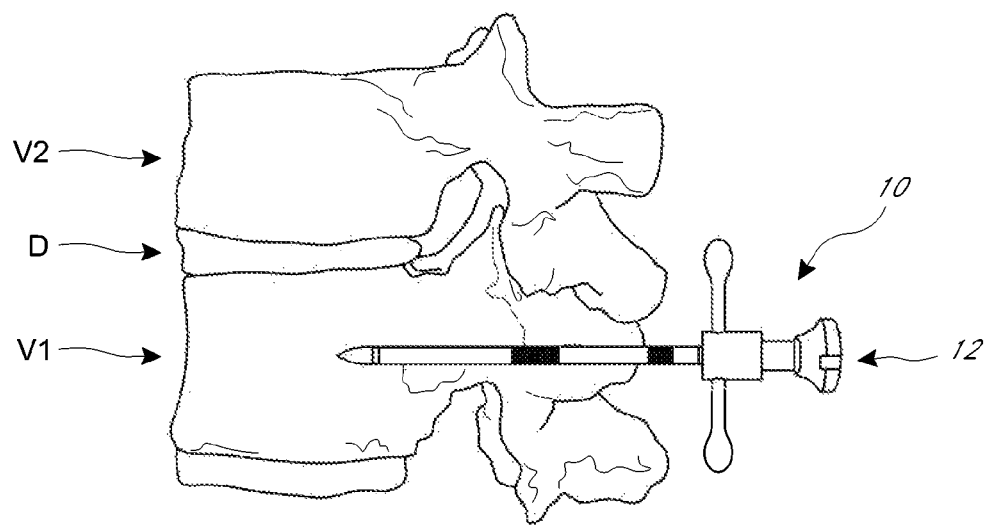
FIGS. 2A-2I illustrate various steps of a method of stabilizing a spine, according to some embodiments.

FIGS. 2A-2I illustrate a method of performing a minimally invasive (e.g., percutaneous) spinal fusion procedure, according to some embodiments of the invention. Access to the first vertebra V1 can be with an unipedicular or bipedicular approach with an access cannula 10, such as a straight cannula about 8, 9, 10, 11, 12, or other gauge in dimension, as illustrated in FIG. 2A. The cannula 10 can be advanced to just beyond the pedicle P into the posterior vertebral body and the inner stylet is then removed.

Figure 2B:
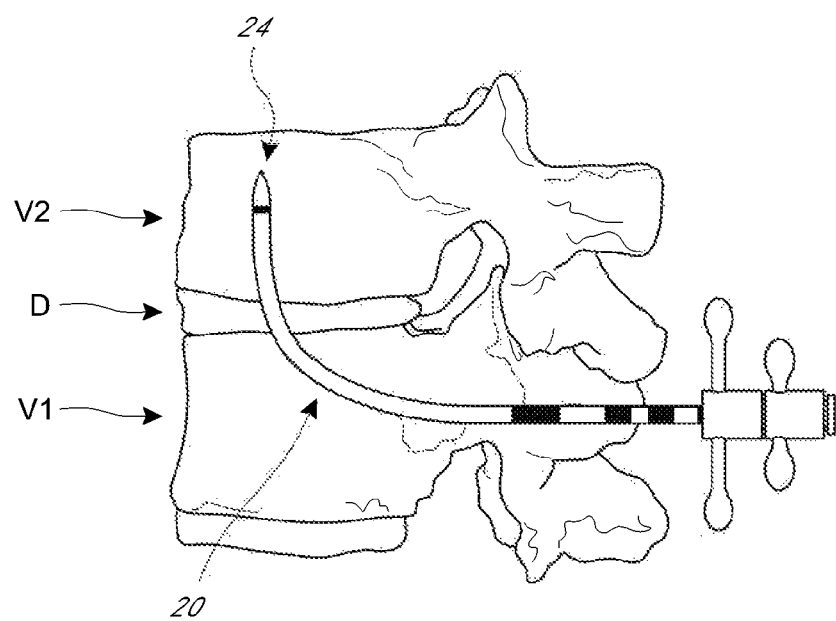

Through the cannula 10, a needle 20, such as a shape memory nitinol needle with a curved unstressed state, such as about 12 gauge in dimension (or 1, 2, 3, 4, or more gauge smaller than the central lumen 12 of the cannula 10 in some cases), would be advanced and the distal end curved in a cephalad direction as shown (or a caudal direction in other embodiments) to cross the intervertebral disc space D into the anterior inferior aspect of the adjacent vertebral body V2, as illustrated in FIG. 2B.

Figure 2C:
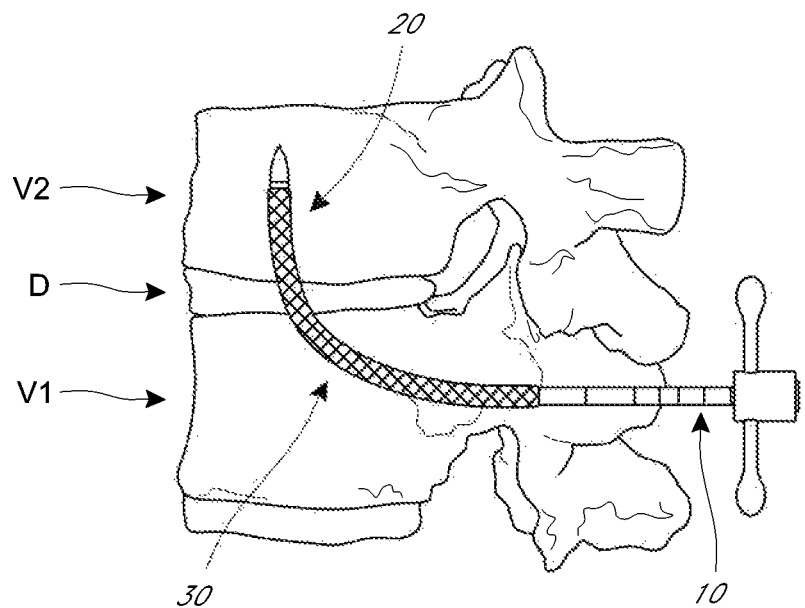
Figure 2D:
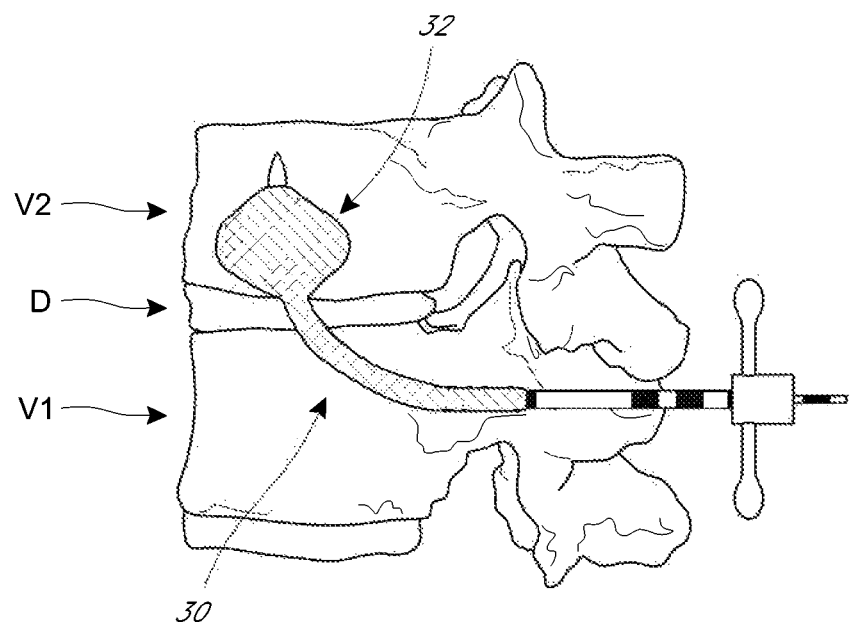
Figure 2E:
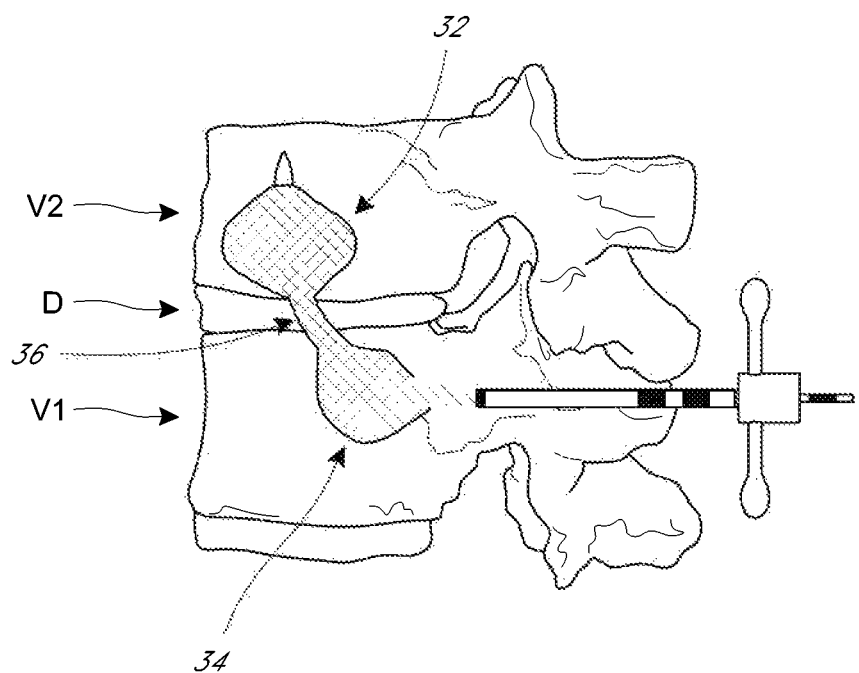
Figure 2F:
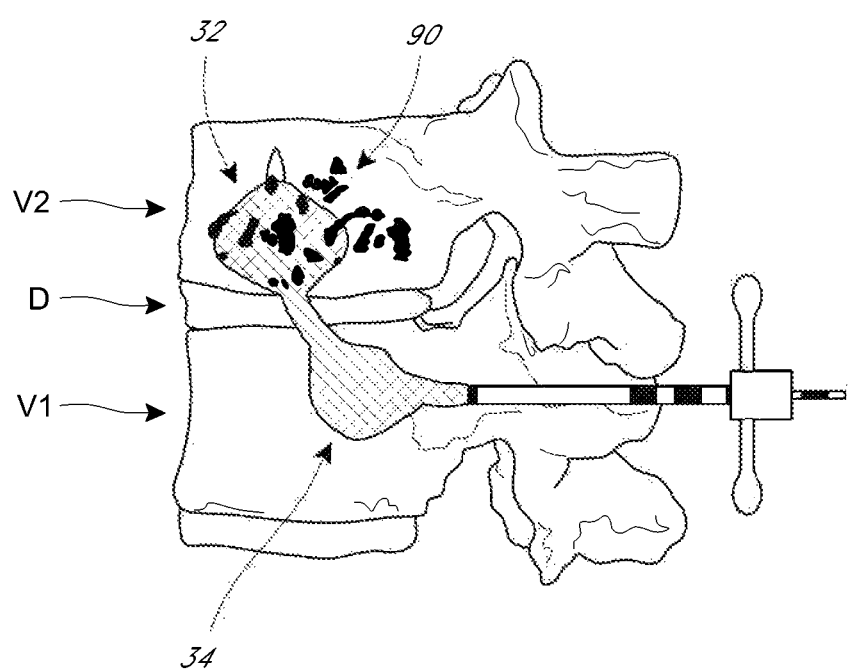

The inner stylet of the nitinol needle 20 can be removed and a stent-like perforated anchor 30, which can be a metal or metal alloy such as a nitinol anchor mounted on a high pressure balloon can be passed through the needle 20 to span the intervertebral disc space D, as illustrated in FIG. 2C. The balloon catheter 41 can be deployed, and the distal end 32 of the anchor 30 in the superior vertebral body V2 can be dilated with the balloon 40 (not shown for clarity) to open up the anchor's interstices (cells), as shown in FIG. 2D. The balloon 40 can be withdrawn into the inferior vertebral body V1 and the proximal portion 34 dilated, as shown in FIG. 2F.

The balloon catheter 41 can be removed and a curvable and/or steerable hollow injection needle 50, such as a nitinol needle having an about 14 gauge dimension in some embodiments can be advanced into the distal end 32 of the anchor 30. In some embodiments, the balloon catheter 41 need not be withdrawn immediately after creating a cavity in either the superior vertebral body V2 or the inferior vertebral body V1 (but can be deflated in some embodiments), and the injection needle 50 can pass through a lumen of the balloon catheter 41, or be integral with the balloon catheter 41 in some embodiments. An appropriate amount of media 90, such as bone cement or other stabilizing material, such as between about 1-5 cc or 2-3 cc, or about 1 cc, 1.5 cc, 2 cc, 2.5 cc, 3 cc, 3.5 cc, 4 cc, 4.5 cc, or 5 cc of PMMA bone cement in some embodiments, can be injected into the distal 32 portion of the anchor 30 under imaging, such as constant fluoroscopic visualization as the cement flows through the interstices of the anchor 30 and into the normal bone marrow space and bony trabeculae, as shown in FIG. 2E. This will stabilize the anchor 30 in place and maximize the surface area contact of cement 90 and bone as the media cures. In some embodiments, the bone cement 90 is injected into cavities within the vertebrae only, and no bone cement 90 or substantially no bone cement 90 resides or migrates into the intervertebral disc space D, either within or outside the central elongate portion 36 of the anchor 30 which is not radially expanded in some embodiments. This can be advantageous in some cases, such that hardened bone cement 90 or other material is not present in the intervertebral disc space D allowing for maintenance of some degree of spinal flexion, extension, and rotation postoperatively. In some embodiments, partial or complete discectomies are not required to be performed during the procedure, to better maintain the intervertebral disc D as mentioned above. However, in some embodiments, the stabilization procedure can be synergistically performed in conjunction with another operative procedure in the same operative session, or within a month, 2 weeks, 1 week, 5, 4, 3, 2, or 1 days, or the same day; either before or after the spinal stabilization procedure, which can be another minimally invasive spinal procedure in some embodiments. For example, one or more discectomies to remove a disc herniation can be performed. In some embodiments, the procedure can also be performed in conjunction with a laminectomy done to decompress the spinal canal (for patients with spinal stenosis), or in conjunction with posterior distraction of the spinous processes to decrease in-folding of the ligamentum flavum and to reduce the amount of neuroforaminal compromise (e.g., the X-STOP procedure from Medtronic, Inc., Minneapolis, Minn.).

Figure 2G:
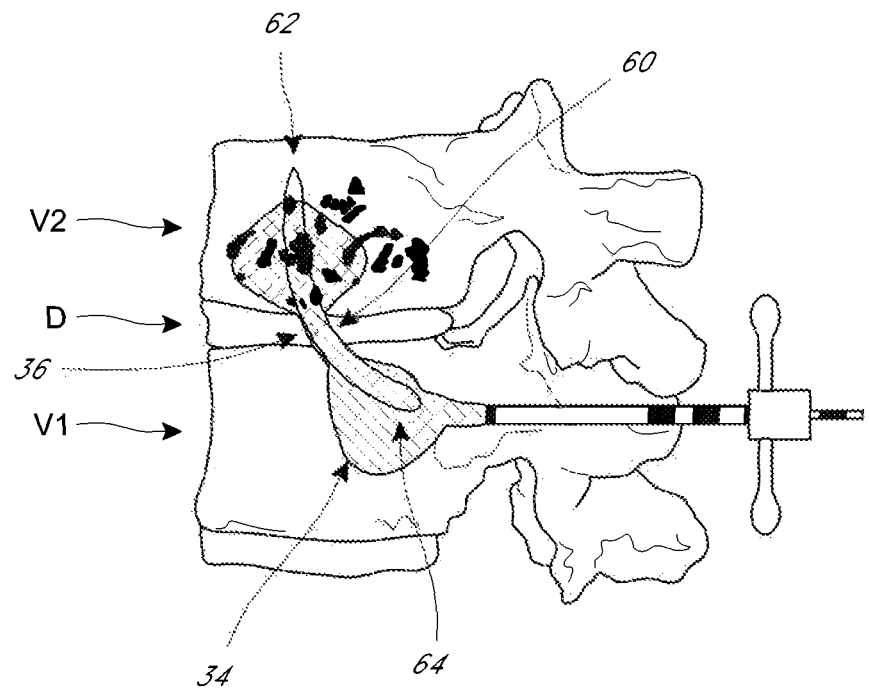
Figure 2H:
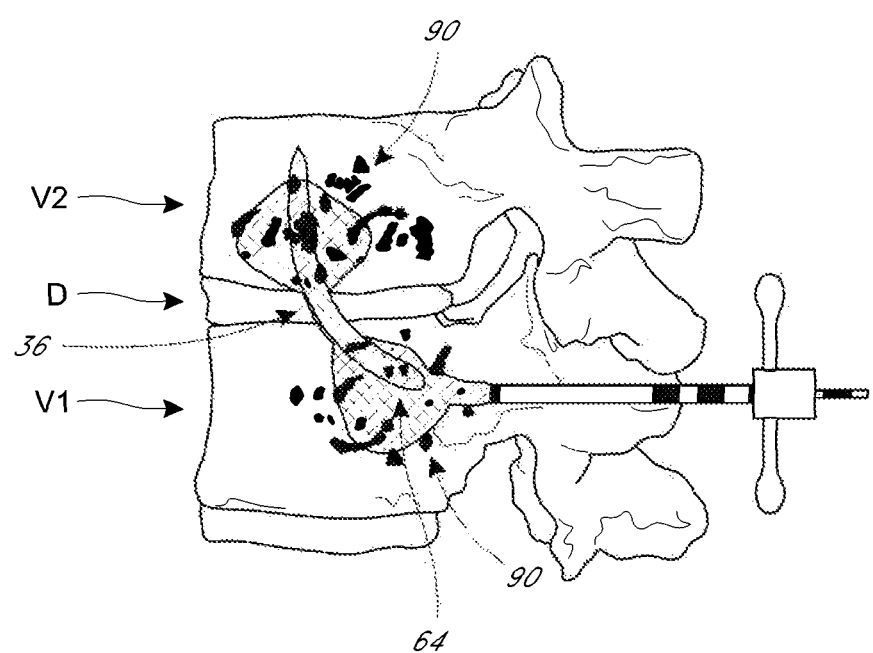

The injection needle 50 can be withdrawn and one, two, or more flexible rods 60, such as an approximately 2 mm in diameter carbon reinforced PEEK curved rod would be placed through the anchor 30 with the distal end 62 of the rod 60 advanced into the cement 90 in the superior vertebral body V2 before the cement has time to solidify, as shown in FIG. 2G. The injection needle 50 could be reintroduced into the proximal dilated end 34 of the anchor 30 in the inferior vertebral body V1 and another volume of media, e.g., about 2-3 cc of PMMA can be injected to imbed the proximal end 64 of the rod 60 in cement 90 and into the cavity, extending into the surrounding bony trabeculae, as shown in FIG. 2H. In some embodiments, the procedure can also advantageously benefit patients who also have a vertebral body compression fracture by restoring or improving the vertebral height of the fractured vertebrae.

Figure 2I:
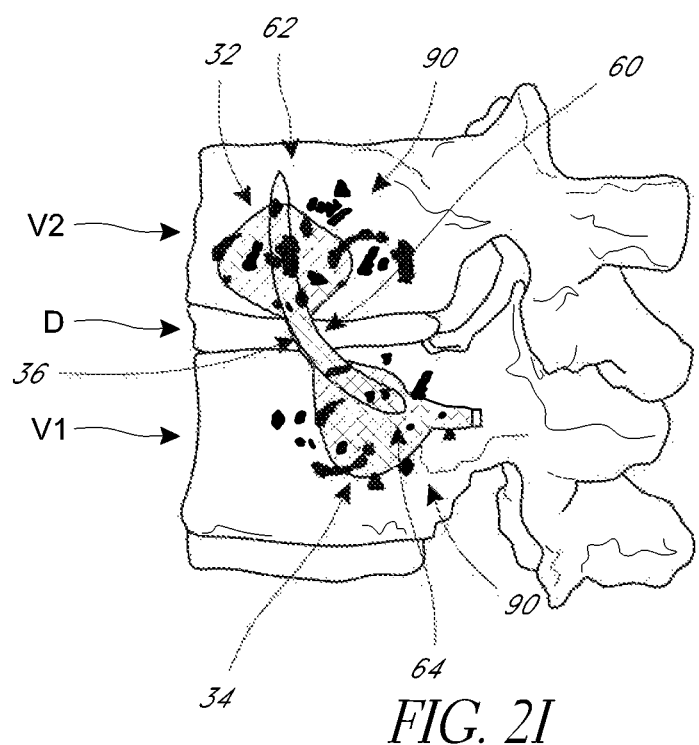

The one, two, or more generally flexible carbon fiber rods 60, which can be generally positioned along the cranial-caudal axis, span the disc space D and can limit translational movement but allow some limited flexion and extension, in contrast to conventional spinal fusions wherein any relative movement of adjacent fused vertebrae may no longer be possible. In some embodiments, multiple rods 60 can be placed side-by-side if additional stabilization is required. The PMMA cement 90 immobilizes the proximal 64 and distal 62 ends of the one or more rods 60 in the adjacent vertebral bodies V2, V1, but the cement 90 can be absent in the central portion 36 of the anchor 30 (e.g., in the intervertebral disc space D; the cement 90 does not extend beyond the vertebral endplates into the disc space D in some embodiments), which advantageously preserves some degree of flexion and extension movement as noted above, such as about, at least about, or no more than about 1, 2, 3, 4, 5, 6, 7, 8, 9, 10, or more degrees of flexion and/or extension, such as between about 1 degree and about 5 degrees, or between about 2 degrees and about 5 degrees in some embodiments. The proximal 64 and/or distal ends 62 of the rods 60 can extend some distance beyond the expanded portions 32, 34 of the anchor 30 filled with bone cement 90 in some embodiments. The anchor 30 limits excessive extension and advantageously prevents loosening, displacement, or other migration of the rod(s) 60. The rods 60 can advantageously further maintain the height of the intervertebral disc space D and prevent the vertebrae V1, V2 from collapsing on each other. An embodiment of a system after implantation and removal of the curvable needle and cannula is illustrated in FIG. 2I. In some embodiments, any number of the foregoing steps can be repeated in order to effect multi-level spinal fusions depending on the desired clinical result.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "accessing a vertebral body" includes "instructing the accessing of a vertebral body." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A method for stabilizing the spine, comprising:
   inserting a tubular body into the interior of the a first vertebral body, through an intervertebral disc, and into the interior of a second vertebral body adjacent the first vertebral body;
   inserting an anchor having interstices through a lumen of the tubular body such that a distal end of the anchor is within the interior of the second vertebral body, a proximal end of the anchor is within the interior of the first vertebral body, and a central portion of the anchor spans the intervertebral disc;
   expanding the distal end of the anchor within the interior of the second vertebral body;
   expanding the proximal end of the anchor within the interior of the first vertebral body;
   flowing a first volume of media into the distal end of the anchor within the interior of the second vertebral body, wherein the media flows through the interstices of the anchor outside the anchor and into the interior of the second vertebral body;
   flowing a second volume of media into the proximal end of the anchor within the interior of the first vertebral body; and
   inserting a rod through the central lumen of the tubular body, such that a distal portion of the rod is positioned within the interior of the second vertebral body and in contact with the first volume of media, the proximal portion of the rod is positioned within the interior of the first vertebral body, and a central portion of the rod spans the intervertebral disc, wherein the rod resides at least partially within an interior of the anchor.

2. The method of claim 1, wherein substantially no media flows within the intervertebral disc.

3. The method of claim 1, wherein the method does not involve a discectomy procedure.

4. The method of claim 1, wherein the media comprises PMMA.

5. The method of claim 1, wherein the first volume of media is between about 1 cc and about 5 cc.

6. The method of claim 1, wherein the rod comprises a carbon fiber material.

7. The method of claim 6, wherein the carbon fiber material comprises PEEK.

8. The method of claim 1, wherein expanding the distal end of the anchor within the interior of the second vertebral body and expanding the proximal end of the anchor within the interior of the first vertebral body comprises expanding a balloon.

9. The method of claim 1, wherein the inserting the anchor step comprises inserting the anchor carried proximate the distal end of a balloon catheter.

10. The method of claim 1, wherein a central portion of the anchor is not expanded, and the distal and proximal expanded portions of the anchor have a maximal expanded diameter that is at least 2× the unexpanded diameter of the central portion of the anchor.

11. The method of claim 1, wherein the anchor comprises a shape memory material.

12. The method of claim 1, wherein the anchor is inserted in a compressed substantially tubular configuration.

13. The method of claim 1, wherein following insertion of the rod the first and second volumes of media harden, fixing the anchor and rod in place.

14. The method of claim 1, wherein flowing the second volume occurs after inserting the rod, such that the proximal portion of the rod is in contact with the second volume of media after flowing the second volume.

15. A system for stabilizing the spine, comprising:
an anchor having a proximal end, a distal end, and a central portion, the anchor having a compressed configuration, and an expanded configuration wherein the proximal end and the distal end of the anchor are expanded while the central portion of the anchor is not expanded, wherein the proximal end and the distal end of the anchor have maximal expanded diameters at their widest portions of greater than the diameter of the central portion of the anchor, wherein the anchor is sized and configured such that the proximal end of the anchor can reside within the interior of a first vertebrae, the distal end of the anchor can reside within the interior of a second vertebrae adjacent the first vertebrae, and the central portion of the anchor spans an intervertebral disc between the first vertebrae and the second vertebrae, wherein the anchor is defined by an expandable frame and interstices within the frame along the axial length of the anchor; a rod dimensioned to fit within an interior of the anchor, such that when implanted the rod is configured to reside substantially within the anchor, wherein the distal end of the rod is configured to reside within the distal end of the anchor within the interior of the second vertebrae, the proximal end of the rod is configured to reside within the proximal end of the anchor within the interior of the first vertebrae and the central portion of the anchor is configured to span an intervertebral disc between the first vertebrae and the second vertebrae;
wherein the anchor is configured such that when the distal end of the anchor is inserted into the interior of the second vertebrae and a volume of media is injected into the distal end of the anchor, the volume of media can flow through the interstices of the anchor outside the anchor and into the interior of the second vertebrae.

16. The system of claim 15, wherein the rod comprises PEEK.

17. The system of claim 15, further comprising a balloon catheter comprising a balloon configured to expand the proximal end and the distal end of the anchor.

18. The system of claim 15, wherein the anchor is carried on a distal end of the balloon catheter.

19. A system for stabilizing the spine, comprising:
an anchor having a proximal end, a distal end, and a central portion, the anchor having a compressed configuration and an expanded configuration, wherein in the expanded configuration the proximal end and the distal end of the anchor have maximal expanded diameters at their widest portions of greater than the diameter of the central portion of the anchor, wherein the anchor is sized and configured such that the proximal end of the anchor can reside within the interior of a first vertebrae, the distal end of the anchor can reside within the interior of a second vertebrae adjacent the first vertebrae, and the central portion of the anchor spans an intervertebral disc between the first vertebrae and the second vertebrae, wherein the anchor is defined by an expandable frame and interstices within the frame along the axial length of the anchor; a rod dimensioned to fit within an interior of the anchor, such that when implanted the rod is configured to reside substantially within the anchor, wherein the distal end of the rod is configured to reside within the distal end of the anchor within the interior of the second vertebrae, the proximal end of the rod is configured to reside within the proximal end of the anchor within the interior of the first vertebrae and the central portion of the anchor is configured to span an intervertebral disc between the first vertebrae and the second vertebrae;
wherein the anchor is configured such that when the distal end of the anchor is inserted into the interior of the second vertebrae and a volume of media is injected into the distal end of the anchor, the volume of media can flow through the interstices of the anchor outside the anchor and into the interior of the second vertebrae.

* * * * *